United States Patent
Tindall

(12) 
(10) Patent No.: US 6,663,830 B1
(45) Date of Patent: Dec. 16, 2003

(54) WOOD CONDITIONER WITH ANTISEPTIC PROPERTIES

(76) Inventor: John R. Tindall, 6537 Joshua St., Oak Park, CA (US) 91377

( * ) Notice: Subject to any disclaimer, the term of this patent is extended or adjusted under 35 U.S.C. 154(b) by 34 days.

(21) Appl. No.: 09/643,632

(22) Filed: Aug. 22, 2000

(51) Int. Cl.$^7$ .................................................. A61L 2/18
(52) U.S. Cl. ........................ 422/28; 424/404; 424/405; 426/665
(58) Field of Search ............................ 422/28; 424/404, 424/405; 426/289–296, 302, 330, 330.4, 665

(56) References Cited

U.S. PATENT DOCUMENTS

| | | | |
|---|---|---|---|
| 5,342,436 A | * | 8/1994 | Thrasher ...................... 106/10 |
| 5,419,908 A | * | 5/1995 | Richter et al. .............. 424/405 |
| 5,753,607 A | * | 5/1998 | Burke et al. ................. 510/242 |
| 5,962,001 A | * | 10/1999 | Rose et al. .................. 424/404 |
| 6,358,623 B1 | * | 3/2002 | Fukushima .................. 428/543 |

* cited by examiner

Primary Examiner—Robert J. Warden, Sr.
Assistant Examiner—Sean E. Conley
(74) Attorney, Agent, or Firm—Stetina Brunda Garred & Brucker

(57) ABSTRACT

Composition and method for simultaneously disinfecting and conditioning a wooden cutting surface, such as a cutting board or counter top. According to a preferred embodiment, the composition comprises a mixture of ethanol and food-grade mineral oil where the ethanol is present in an amount sufficient impart antiseptic properties. To the extent desired, other adjuvants, such as flavor enhancers, coloring agents, and the like may be added. The method comprises contacting the wooden cutting surface with such composition for a time sufficient to enable the ethanol to adequately disinfect the cutting surface. Preferably, such method may be performed by merely spraying or wiping the composition directly onto the wooden cutting surface.

8 Claims, No Drawings

WOOD CONDITIONER WITH ANTISEPTIC PROPERTIES

BACKGROUND OF THE INVENTION

Wooden cutting boards for cutting food are well-known and utilized extensively. In this regard, such cutting boards provide a solid, heavy-duty surface upon which food items, and in particular vegetables, fruits, and meats, can be cut to desired dimensions or portions. Advantageously, the wood surface provides sufficient durability to serve as a cutting surface without damaging the steel knife blades typically utilized to cut the food items. Indeed, but for the typical wear and tear associated with repeated cuttings, wooden cutting boards can be used indefinitely. Along these lines, due to the attractiveness and durability of wood, such cutting boards are frequently incorporated as countertop surfaces in kitchens and the like to thus provide a readily accessible surface upon which food may be cut.

Notwithstanding their advantages, wooden cutting boards and counter tops suffer from numerous drawbacks. Perhaps most serious of such drawbacks is the ability of such counter top surfaces to harbor communicable diseases capable of causing food poisoning. As is well-known, due to the porous nature of wood—coupled with the repetition by which the same comes into contact with raw food—serious and sometimes life-threatening food poisoning can be caused by a variety of pathogens that exist upon such surfaces. Examples of such pathogens include escherichia coli, normally found in undercooked and/or ground red meat; salmonella, which is typically found in chicken meat products; spiralis, found in raw or inadequately cooked or processed pork or pork products responsible and for causing trichinosis; and hepatitis A virus, responsible for producing hepatitis A, which may be found in contaminated raw shell fish. To a lesser extent, such surfaces can facilitate communicable diseases transmitted via person to person. For example, influenza and ammonia are but two of a multitude of dehabilitating conditions caused by pathogens that can exist and be transmitted across wooden cutting surfaces.

While disinfectants and anti-microbial cleaners are well-known and readily available to disinfect such wood cutting surfaces, the use of such cleaning compositions is typically undesirable. In this regard, such compositions frequently employ harsh cleaning agents that, although effective in killing microorganisms, are toxic in and of themselves. As such, it is often necessary to immediately rinse off the wood cutting surfaces or wash away the residues left by such cleaners following their application, which in essence requires that such surfaces be cleaned twice. Furthermore, great care must be exercised in utilizing such cleaners so that the same are not inadvertently applied to food substances that are placed in close proximity to such cutting surfaces.

Separate and apart from the potential toxicities of such cleaning agents are the deleterious effects the same have on the wood itself. Because of their caustic nature, most cleaning agents in use can and frequently do dry-out the wood surface and cause the same to assume unsightly appearance over time. In this regard, such cleaning agents, including non-toxic cleaning agents such as regular soap, cause wood to fade and eventually become brittle. The latter effect is especially problematic insofar as the brittleness imparted to the wood causes the wood to lose strength over time. As such, when subjected to repeated cuttings, the wood can and does scratch more easily and can even splinter in certain circumstances.

Accordingly, there is a substantial need in the art for a composition and method for disinfecting a wooden cutting board or countertop that, in addition to effectively eradicating potentially disease-causing pathogens, further preserves and protect the underlying wood cutting surface. There is further a need in the art for such a composition and method that is non-toxic and safe for the environment. Moreover, there is a need in the art for such a composition and method that, in addition to the foregoing properties, is relatively inexpensive to manufacture, is of simple formulation, and may be readily produced using commercially-available materials.

SUMMARY OF THE INVENTION

The present invention specifically addresses and alleviates the above-identified deficiencies in the art. In this regard, the present invention is directed to a composition and method for simultaneously disinfecting and conditioning a wood cutting surface. Advantageously, the composition and method of the present invention safely and easily cause a wooden cutting surface to be readily disinfected but without subjecting the wood to oxidizing compounds that would otherwise cause the same to dry out and assume an unsightly appearance, as do conventional cleaning agents and the like.

According to a preferred embodiment, the composition comprises a mixture of ethanol in combination with food-grade mineral oil. The composition is preferably formed such that the ethanol is present in an amount sufficient to provide antiseptic properties, with the remainder constituting the mineral oil. Presently, it is believed that the ethanol component may be present in an amount from 40% to 99% by volume, with the mineral oil being present in an amount from 60% to 1% by volume. In a more highly preferred embodiment, the ethanol is present in an amount from 60 to 90% by volume with the mineral oil being present in a corresponding amount of 30 to 10% by volume. In a most highly preferred embodiment, the ethanol component is present in an amount ranging from 65% to 85% whereas the mineral oil component is present in an amount from 35% to 15% by volume. To the extent desired, additional components may be added, such as a flavor enhancer, coloring agent, preservative, buffering agent, anti-oxidant, fragrance, and/or sequestering agent, to name a few. Water may additionally be added to the extent necessary to produce a desired concentration of the composition.

It is therefore an object of the present invention to provide a composition and method for disinfecting a wooden cutting surface that, rather than harming the wood as a result of such disinfecting process, preserves and conditions the wood to thus enhance the care thereof.

Another object of the present invention is to provide a composition and method for disinfecting a wooden cutting surface that can rapidly eradiate substantially all pathogens present upon a wooden cutting surface.

Another object of the present invention is to provide a composition and method for disinfecting a wooden cutting surface that can effectively eradicate pathogens present on a cutting surface that is of minimal toxicity to humans and poses no threat to the environment.

Another object of the present invention is to provide a composition and method for disinfecting a wooden cutting surface that can increase the lifespan of the wooden cutting surface.

Still further object of the present invention is to provide a composition and method for disinfecting a wooden cutting surface that is easy to utilize, may be readily formulated from existing materials, is inexpensive to formulate, and is substantially safer, more efficient and less expensive then prior art compositions and methods.

DETAILED DESCRIPTION OF A PREFERRED EMBODIMENT

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

The present invention is directed to a composition and method for simultaneously disinfecting and conditioning a wooden cutting surface, such as wooden cutting boards, counter tops, and the like upon which foods are cut and handled. In this regard, the present invention is specifically directed toward compositions and methods that can disinfect such surfaces, such that the same pose little, if any, threat of transmitting pathogens present upon food items, and in particular pathogens present in raw or under-cooked meat and shellfish, while simultaneously preserving the look and quality of the wood surface.

According to a preferred embodiment, the composition comprises a mixture of food-grade mineral oil and ethanol, the latter being present in an amount sufficient to impart disinfecting properties. In this regard the use of alcohol, and in particular ethanol, for use as a disinfecting agent is well-known and widely utilized. As shown in Table 1, the basic two (2) components that comprise the invention and the respective percentages by volume thereof will encompass the following ranges:

TABLE 1

| COMPONENTS | PERCENT BY VOLUME |
|---|---|
| Ethanol | 40% to 99% |
| Mineral Oil | 60% to 01% |

It is to be understood that the percentages of the two (2) components above will total 100% by volume. If other materials are included in the formulation, the percentages of all ingredients will obviously total 100% by volume.

The ethanol component preferably comprises commercially-available, high grade ethyl alcohol, and may constitute such grades known in the art as grain alcohol or high-purity alcohol. Due to the fact that the compositions of the present invention may inadvertently be consumed by virtue of the close proximity by which the same may be applied to food items, it is important to realize that such commercially-available alcohol will be devoid of denaturants, such as methyl alcohol, pyridine, benzine, pine oil, benzene, and hydrogenated organic compounds, typically added to ethanol to ensure non-beverage/non-food usage.

The mineral oil component will likewise be of a high-grade, commercially-available variety. In this respect, it is important to emphasize that the mineral oil component must be suitable for human consumption due to the likelihood the composition will be applied in close proximity to food items. Currently, it should be recognized that food grade mineral oil, while commercially available, it still unregulated. Notwithstanding, any reputable food grade mineral oil currently available that may be procured commercially may be utilized in the practice of the present invention.

In a more highly refined embodiment, there is shown in Table 2, the respective percentages by volume of the two (2) components of the composition of the present invention.

TABLE 1

| COMPONENTS | PERCENT BY VOLUME |
|---|---|
| Ethanol | 40% to 99% |
| Mineral Oil | 60% to 01% |

As discussed above, both components, namely, the ethanol and mineral oil will be of high-grade quality and suitable for human consumption.

In a most highly preferred embodiment, there is shown in Table 3 the respective percentages by volume of the two (2) components of the present invention:

TABLE 3

| COMPONENTS | PERCENT BY VOLUME |
|---|---|
| Ethanol | 65% to 85% |
| Mineral Oil | 35% to 15% |

Again, both components will be of commercial, high-grade quality. Along these lines, with respect to the ethanol component, the same will be of beverage quality and devoid of any denaturants.

As will be appreciated by those skilled in the art, the composition of the present invention advantageously omits the use of any toxic chemicals typically found in most cleaning solutions for use as disinfecting agents. Indeed, most cleaning preparations currently in use, albeit effective, pose a threat in and of themselves by introducing toxic, oxidizing agents that can and frequently do come into close proximity to food that is ultimately consumed. In fact, it is common to practice throughly wash down a cutting board surface following application of such conventional cleaning/disinfecting preparations to thus make the cutting surface safe for its intended use (i.e., food cutting and preparation).

As will be recognized, the ethanol component is responsible for providing the disinfectant properties of the composition of the present invention. As is well-known, ethyl alcohol has been widely used as a disinfecting agent. The mineral oil component, on the other hand, advantageously provides a mechanism for preserving and enhancing the appearance of the wood cutting board. As will be appreciated by those skilled in the art, the mineral oil acts to lubricate and condition the wood surface such that the same does not dry out, which can cause the same to assume an unsightly appearance over time. Indeed, because of the drying effect imparted by most conventional cleaning agents, such wooden surfaces tend to become unsightly after only a few cleanings. Moreover, such drying effect is known to cause such wooden cutting surfaces to splinter and wear down more rapidly over time. As such, the mineral oil component, in addition to being non-toxic (not to mention edible), naturally provides a way to enhance the appearance of the cutting surface. As will be recognized, there has not hereto been available such a composition capable of simultaneously performing such functions, namely, disinfection coupled with wood conditioning.

Although not essential, it is further contemplated that adjuvants may be added to further enhance the performance or stabilize the basic two (2) component formulation. Representative examples include buffering agents that buffer within a desired pH range (e.g., pH 4–8), anti-oxidants, sequestering agents, preservatives, fragrances, flavor enchanters, and/of coloring agents. In some applications it may even be desired to include an additional anti-microbial agent. Likewise, as may be necessary to achieve a certain formulation, it is contemplated that water may additionally be added as component, particularly with respect to the ethanol component, to thus enable the same to remain present at a fixed amount of volume. Along these lines, it is contemplated that water may be present in an amount from 2% up to 55% by volume of the resultant compositions.

The method of using the composition of the present invention involves applying the aforementioned embodiments to the wooden cutting surface sought to be treated. In this regard, it is believed that such composition need only be sprayed or lightly misted upon the surface sought to be treated and thereafter allowed to stand for approximately 30 seconds. Alternatively, the composition may be poured upon such wooden cutting surface and thereafter wiped or buffed. As will be recognized by those skilled in the art, due to the volatile nature of ethanol, coupled with the high concentration of such substance present within the composition, great care must be taken to ensure the same does not come into contact with open flame or any other type of igniting apparatus, such as lighters, gas stoves, and the like.

There has thus then provided a composition and method for disinfecting a wooden cutting surface while simultaneously conditioning the same. Although the invention has been described herein with specific reference to presently preferred embodiments thereof, it will be appreciated by those skilled in the art that various additions, modifications, deletions, and alterations may be made to such embodiments without departing from the spirit and scope of the invention. For example, as opposed to a mineral oil, it is contemplated that other types of oil such as olive oil, vegetable oil, and other well-known cooking oils may possibly be substituted thereinstead, which may thus impart the desired wood-protecting properties. Accordingly, it is intended that all reasonably foreseeable additions, modifications, deletions, and alterations be included within the scope of the invention as defined in the following claims.

What I claim is as follows:

1. A composition for simultaneously disinfecting and conditioning a wooden cutting surface for cutting food consisting essentially of:
   a) a food-grade mineral oil present in an amount ranging from 10% to 40% by volume of said composition;
   b) ethanol, said ethanol being present in an amount ranging from 60% to 90% by volume of said composition: and
   c) wherein said composition is edible and suitable for human consumption.

2. The composition of claim 1 wherein:
   a) said mineral oil is present in an amount ranging from 15% to 35% by volume of said composition; and
   b) said ethanol present in an amount from 65% to 85% by volume by volume of said composition.

3. The composition of claim 1 further including an adjuvant selected from the group consisting of a buffering agent, an anti-oxidant, a sequestering agent, a fragrance, a flavor enhancer, and a coloring agent.

4. The composition of claim 3 wherein said adjuvant is further selected from the group consisting of an anti-microbial agent.

5. A method for simultaneously disinfecting and conditioning a wooden cutting surface for cutting food, the method comprising of steps:
   a) providing an edible composition suitable for human consumption consisting essentially of mineral oil present in an amount ranging from 10% to 40% by volume of the composition and ethanol present in an amount from 60% to 90% by volume of the composition; and
   b) contacting said wooden surface with said composition provided for in step a).

6. The method of claim 5 wherein in step a), said composition comprises:
   a) mineral oil present in an amount ranging from 15% to 35% by volume of said composition; and b) said ethanol present in an amount from 65% to 85% by volume of such composition.

7. The method of claim 5 wherein in step b), said composition is sprayed upon said wooden cutting surface.

8. The method of claim 5 wherein in step b), said composition is poured upon said wooden cutting surface.

* * * * *